United States Patent
Kunardi et al.

(10) Patent No.: US 11,931,148 B2
(45) Date of Patent: Mar. 19, 2024

(54) CATHETER SYSTEM TO FACILITATE BLOOD SAMPLING AND RELATED METHODS

(71) Applicant: Becton, Dickinson and Company, Franklin Lakes, NJ (US)

(72) Inventors: Linda Kunardi, Serangoon (SG); Kiat Jin Cheng, Bishan (SG)

(73) Assignee: Becton, Dickinson and Company, Franklin Lakes, NJ (US)

( * ) Notice: Subject to any disclaimer, the term of this patent is extended or adjusted under 35 U.S.C. 154(b) by 369 days.

(21) Appl. No.: 16/997,526

(22) Filed: Aug. 19, 2020

(65) Prior Publication Data

US 2021/0068729 A1    Mar. 11, 2021

Related U.S. Application Data

(60) Provisional application No. 62/898,374, filed on Sep. 10, 2019.

(51) Int. Cl.
  *A61B 5/15*   (2006.01)
  *A61M 25/06*  (2006.01)
  *A61M 39/10*  (2006.01)

(52) U.S. Cl.
  CPC .... *A61B 5/150213* (2013.01); *A61B 5/15003* (2013.01); *A61B 5/150236* (2013.01);
  (Continued)

(58) Field of Classification Search
  CPC .......... A61B 5/15003; A61B 5/150267; A61B 5/150213; A61B 5/150236;
  (Continued)

(56) References Cited

U.S. PATENT DOCUMENTS 4,193,400 A * 3/1980 Loveless .......... A61M 25/0693
                                                    138/40
4,370,987 A * 2/1983 Bazell ............. A61B 5/150526
                                                    600/573

(Continued)

FOREIGN PATENT DOCUMENTS

CA    2203348    * 11/1997
GB    2508466      6/2014

(Continued)

*Primary Examiner* — Yi-Shan Yang
*Assistant Examiner* — Om Patel
(74) *Attorney, Agent, or Firm* — Kirton McConkie; Whitney Blair; Kevin Stinger (57) ABSTRACT

A catheter system may include a catheter assembly, which may include a catheter adapter and a catheter extending distally from a distal end of the catheter adapter. The catheter system may also include a needle assembly, which may include a needle hub and an introducer needle. The needle hub may include: a distal end coupled to the proximal end of the catheter adapter; a proximal end; a wall disposed between the distal end of the needle hub and the proximal end of the needle hub; and a flashback chamber proximate the wall. The introducer needle may be press-fit within a through-hole of the wall. The catheter system may also include a plug coupled to the proximal end of the needle hub. A blood collection device may be coupled to a proximal end of the plug to collect blood from a patient.

19 Claims, 9 Drawing Sheets

(52) U.S. Cl.
CPC .. *A61B 5/150351* (2013.01); *A61B 5/150732* (2013.01); *A61B 5/150992* (2013.01); *A61M 25/0606* (2013.01); *A61M 25/0693* (2013.01); *A61M 39/10* (2013.01); *A61M 2039/1077* (2013.01)

(58) Field of Classification Search
CPC ........ A61B 5/150389; A61B 5/150732; A61B 5/150633; A61B 5/150641; A61B 5/150648; A61B 5/150656; A61B 5/150351; A61B 5/150992; A61B 5/15074; A61B 5/153; A61B 5/15; A61B 5/150015; A61B 5/150022; A61B 5/15019; A61B 5/150206; A61B 5/150251; A61B 5/150274–297; A61B 5/150354; A61M 25/06–0637; A61M 25/065; A61M 25/0693; A61M 39/10; A61M 2039/1077; A61M 39/02–06; A61M 39/26; A61M 39/0247; A61M 39/20; A61M 2039/0202; A61M 2039/0205; A61M 2039/0258; A61M 2039/027; A61M 2039/205; A61M 2025/0092
See application file for complete search history.

(56) References Cited

U.S. PATENT DOCUMENTS

| | | | | |
|---|---|---|---|---|
| 5,032,116 | A * | 7/1991 | Peterson | A61M 25/0693 604/168.01 |
| 5,685,855 | A * | 11/1997 | Erskine | A61M 25/0693 604/110 |
| 2001/0018572 | A1 | 8/2001 | Kinsey et al. | |
| 2011/0046570 | A1 | 2/2011 | Stout et al. | |
| 2016/0361519 | A1 * | 12/2016 | Teoh | A61M 25/0606 |
| 2017/0120010 | A1 * | 5/2017 | Burkholz | A61M 39/0606 |

FOREIGN PATENT DOCUMENTS

| | | | |
|---|---|---|---|
| JP | 2000116791 | 4/2000 | |
| WO | WO-9907431 A1 * | 2/1999 | ........ A61M 25/0606 |
| WO | WO-2007041450 A2 * | 4/2007 | ........ A61M 25/0009 |
| WO | 2016/007442 | 1/2016 | |
| WO | 2017/074684 | 5/2017 | |
| WO | 2019/008432 | 1/2019 | |

* cited by examiner

CATHETER SYSTEM TO FACILITATE BLOOD SAMPLING AND RELATED METHODS

RELATED APPLICATIONS

This application claims the benefit of U.S. Provisional Patent Application No. 62/898,374, filed Sep. 10, 2019, and entitled CATHETER SYSTEM TO FACILITATE BLOOD SAMPLING AND RELATED METHODS which is incorporated herein in its entirety.

BACKGROUND

Intravenous catheters are commonly used for a variety of infusion therapies. For example, intravenous catheters may be used for infusing fluids, such as normal saline solution, various medicaments, and total parenteral nutrition, into a patient. Intravenous catheters may also be used for withdrawing blood from the patient.

Common types of intravenous catheter are peripheral IV catheters ("PIVCs"), peripherally inserted central catheters ("PICCs"), and midline catheters. Intravenous catheters may include "over-the needle" catheters, which may be mounted over a needle having a sharp distal tip. The sharp distal tip may be used to pierce skin and the vasculature of the patient. Insertion of the intravenous catheter into the vasculature may follow the piercing of the vasculature by the needle. The needle and the intravenous catheter are generally inserted at a shallow angle through the skin into the vasculature of the patient with a bevel of the needle facing up and away from the skin of the patient.

In order to verify proper placement of the introducer needle and/or the intravenous catheter in the vasculature, a user generally confirms that there is flashback of blood, which may be visible to the user. In some instances, the introducer needle may include a notch disposed towards a distal end of the introducer needle, and in response to the distal tip of the introducer needle being positioned within the vasculature, blood may flow proximally through a needle lumen, exit the needle lumen through the notch, and then travel proximally between an outer surface of the introducer needle and an inner surface of the intravenous catheter.

Accordingly, where the intravenous catheter is at least partially transparent, the user may visualize a small amount of blood "flashback" and thereby confirm placement of the intravenous catheter within the vasculature. Presence of a vasculature entrance indicator, such as flashback, may facilitate successful placement of intravenous catheters. Once placement of the introducer needle within the vasculature has been confirmed, the user may temporarily occlude flow in the vasculature and withdraw the introducer needle, leaving the intravenous catheter in place for future blood withdrawal and/or fluid infusion.

The subject matter claimed herein is not limited to embodiments that solve any disadvantages or that operate only in environments such as those described above. Rather, this background is only provided to illustrate one example technology area where some implementations described herein may be practiced.

SUMMARY

The present disclosure generally relates to devices, systems, and methods to facilitate blood sampling. In some embodiments, a catheter system may include a catheter assembly, which may include a catheter adapter and a catheter. In some embodiments, the catheter adapter may include a distal end, a proximal end, and a lumen extending through the distal end of the catheter adapter and the proximal end of the catheter adapter. In some embodiments, the catheter may be secured within the catheter adapter and may extend distally from the distal end of catheter adapter.

In some embodiments, the catheter system may include a needle assembly, which may include a needle hub, which may include a distal end coupled to the proximal end of the catheter adapter. In some embodiments, the needle hub may include a proximal end and a flashback chamber extending through the proximal end of the needle hub. In some embodiments, the needle hub may include a through-hole disposed at a distal end of the flashback chamber. In some embodiments, an introducer needle may be press-fit within the through-hole.

In some embodiments, the catheter system may include a plug coupled to the proximal end of the needle hub. In some embodiments, the plug may plug a proximal opening of the flashback chamber and provide venting of the flashback chamber. In some embodiments, the plug may include a distal end, a proximal end, a lumen extending through the distal end of the plug and the proximal end of the plug, and a tubular section disposed between the distal end of the plug and the proximal end of the plug. In some embodiments, the distal end of the plug may include a neck portion and a skirt, which may each extend from the tubular section to define an annular channel between the skirt and the neck portion.

In some embodiments, the neck portion may be inserted into the proximal end of the needle hub. In some embodiments, an outer surface of the neck portion may include one or more air vent channels, which may be configured to provide venting of the flashback chamber. In some embodiments, the proximal end of the plug may include a luer adapter. In some embodiments, the proximal end of the plug may include a septum, which may be disposed within the luer adapter.

In some embodiments, the septum may include a resiliently deformable piston element. In some embodiments, the piston element may include a piston head coupled to one or more bellows. In some embodiments, the piston head may include a slit or bore.

In some embodiments, the septum may include a proximal portion, which may be disposed outside the luer adapter. In some embodiments, the septum may include a distal portion, which may extend across the tubular section. In some embodiments, the septum may include an intermediate portion, which may be disposed between the proximal portion and the distal portion. In some embodiments, the septum may include a slit, which may extend longitudinally through the proximal portion, the distal portion, and the intermediate portion. In some embodiments, a cross-section of the proximal portion, the distal portion, and the intermediate portion may form a general H-shape.

In some embodiments, a portion of a wall of the tubular section may include a hole, which may extend through the wall. In some embodiments, a hydrophobic membrane may be disposed within the hole towards an outside of the plug. In some embodiments, a hydrophilic membrane may be disposed within the hole towards an inside of the plug and/or proximate the hydrophobic membrane. In some embodiments, the hydrophilic membrane may prevent fluid leakage through the hole, and the hydrophobic membrane may provide venting of the flashback chamber. In some embodiments, the hole may be distal to the distal portion of the septum.

In some embodiments, as an alternative to the hydrophobic membrane and the hydrophilic membrane, a porous membrane may be disposed within the hole. In some embodiments, the porous membrane may be configured to pass air but not blood.

In some embodiments, a distal end of the catheter may include a notch configured to receive blood. In some embodiments, the notch may be in fluid communication with the flashback chamber. In some embodiments, the needle assembly may include a grip extending outwardly from the needle hub and distal to the distal end of the needle hub. In some embodiments, the introducer needle may include multiple inner diameters.

In some embodiments, a method of blood sampling or collecting blood may include inserting the catheter system into vasculature of a patient. In some embodiments, the method may include coupling a blood collection device to the proximal end of the plug. In some embodiments, the method may include collecting blood from the vasculature within the blood collection device. In some embodiments, the method may include priming the catheter system prior to insertion of the catheter system into the vasculature. In some embodiments, the distal end of the catheter may include the notch in fluid communication with the flashback chamber, and the blood from the vasculature may be collected within the blood collection device without a discard blood sample.

It is to be understood that both the foregoing general description and the following detailed description are examples and explanatory and are not restrictive of the invention, as claimed. It should be understood that the various embodiments are not limited to the arrangements and instrumentality shown in the drawings. It should also be understood that the embodiments may be combined, or that other embodiments may be utilized and that structural changes, unless so claimed, may be made without departing from the scope of the various embodiments of the present invention. The following detailed description is, therefore, not to be taken in a limiting sense.

BRIEF DESCRIPTION OF THE SEVERAL VIEWS OF THE DRAWINGS

Example embodiments will be described and explained with additional specificity and detail through the use of the accompanying drawings in which.

DESCRIPTION OF EMBODIMENTS

All examples and conditional language recited herein are intended for pedagogical objects to aid the reader in understanding the invention and the concepts contributed by the inventor to furthering the art, and are to be construed as being without limitation to such specifically recited examples and conditions. Although embodiments of the present inventions have been described in detail, it should be understood that the various changes, substitutions, and alterations could be made hereto without departing from the spirit and scope of the invention.

Figure 1A:
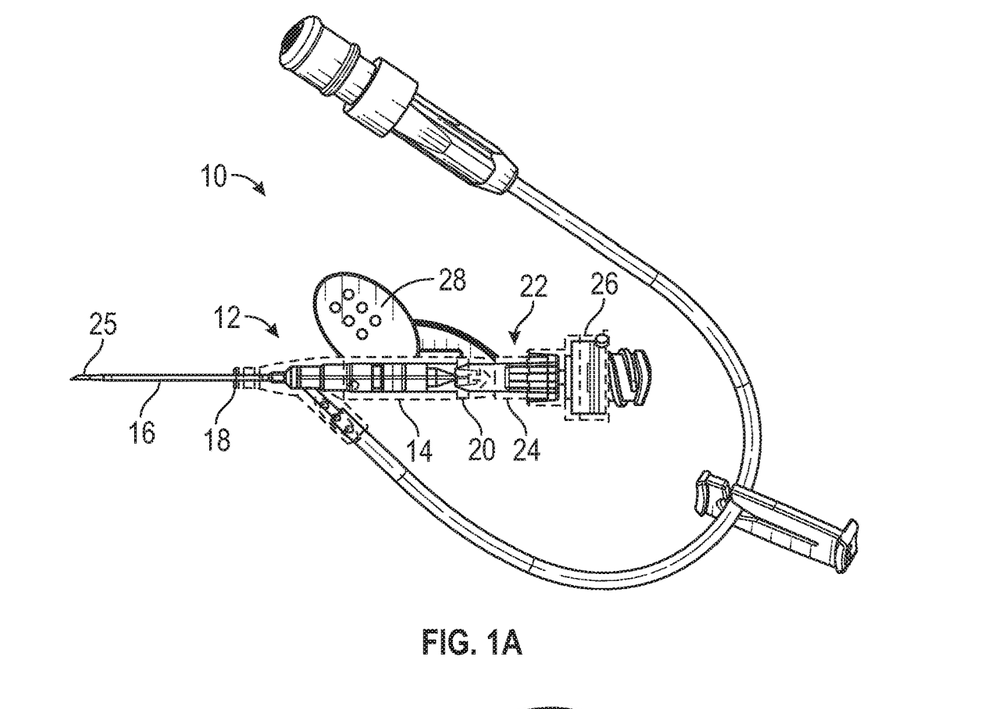
FIG. 1A is an upper perspective view of an example catheter system in an insertion configuration ready for insertion into a patient, according to some embodiments.
Figure 1B:
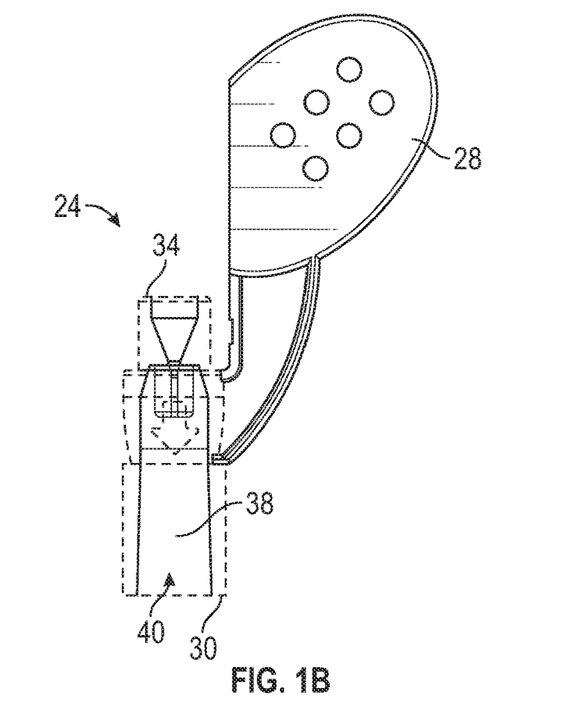
FIG. 1B is an upper perspective view of an example needle hub, with an example introducer needle removed, according to some embodiments.
Figure 1C:
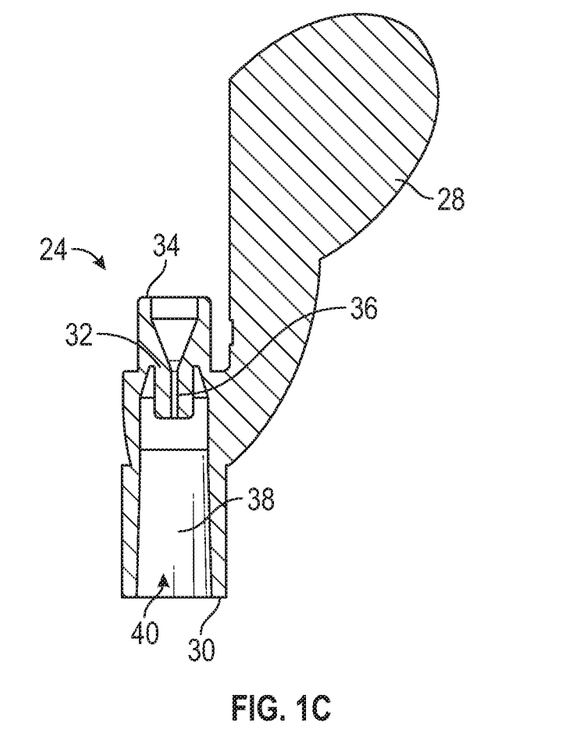
FIG. 1C is a cross-sectional view of the needle hub of FIG. 1B, according to some embodiments.
Figure 1D:
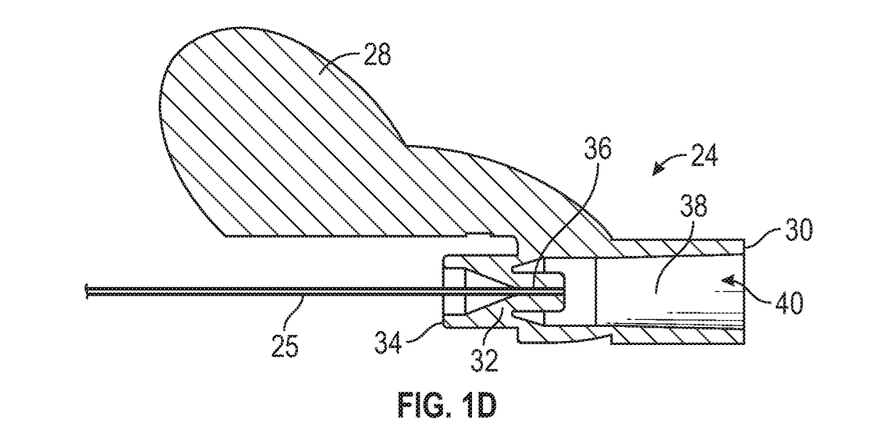
FIG. 1D is a cross-sectional view of the needle hub of FIG. 1B, illustrating the introducer needle press-fit within an example through-hole of the needle hub, according to some embodiments.

Referring now to FIG. 1A, in some embodiments, a catheter system 10 may include a catheter assembly 12, which may include a catheter adapter 14 and a catheter 16. In some embodiments, the catheter adapter 14 may include a distal end 18, a proximal end 20, and a lumen extending through the distal end 18 and the proximal end 20. In some embodiments, the catheter 16 may be secured within the catheter adapter 14 and may extend distally from the distal end 18 of catheter adapter 14.

In some embodiments, the catheter system 10 may include a needle assembly 22, which may include a needle hub 24. In some embodiments, the needle hub 24 may include a distal end coupled to the proximal end 20 of the catheter adapter 14. In some embodiments, the needle assembly 22 may include an introducer needle 25, which may extend through the catheter 16 when the catheter system 10 is in an insertion configuration, ready for insertion into vasculature of a patient.

In some embodiments, the introducer needle 25 may include a sharp distal tip, which may aid in piercing the vasculature. In some embodiments, the catheter system 10 may include a plug 26 coupled to the proximal end of the needle hub 24. In some embodiments, the needle assembly 22 may include a grip 28, which may extend outwardly from the needle hub 24 and distal to the distal end of the needle hub 24.

In some embodiments, the catheter system 10 may include a peripheral intravenous catheter system ("PIVC"), such as, for example, the BD NEXIVA™ Closed IV Catheter system, the BD CATHENA™ Catheter system, the BD VENFLON™ Pro Safely Shielded IV Catheter system, the BD NEOFLON™ IV Cannula system, the BD INSYTE™ AUTOGUARD™ BC Shielded IV Catheter system, or another suitable peripheral intravenous catheter system. In some embodiments, the catheter system 10 may include a peripherally-inserted central catheter ("PICC) system or a midline catheter system.

Referring now to FIGS. 1B-1F, in some embodiments, the needle hub 24 may include a proximal end 30. In some embodiments, the needle hub 24 may include a wall 32, which may be disposed at the distal end 34 of the needle hub 24 or between the distal end 34 of the needle hub 24 and the proximal end 30 of the needle hub 24. In some embodiments, the needle hub 24 may include a through-hole 36. In some embodiments, the needle hub 24 may include a flashback chamber 38, which may extend through the proximal end 30 of the needle hub 24. In some embodiments, the through-hole 36 may be disposed at a distal end of the flashback chamber 38. In some embodiments, the wall 32 may include the through-hole 36. In some embodiments, flashback chamber 38 may be proximate the wall 32. In some embodiments, the needle hub 24 may be transparent, which may allow visualization of blood within the flashback chamber 38.

In some embodiments, the introducer needle 25 may be press-fit within the through-hole 36. In further detail, in some embodiments, an outer diameter of a proximal end of the introducer needle 25 may be slightly greater than a diameter of the through-hole 36 such that the introducer needle 25 and the through-hole 36 interfere with each other. In some embodiments, a proximal end of the introducer needle 25 may be disposed within the flashback chamber 38, such that in response to insertion of the introducer needle 25 within the vasculature of the patient, blood may flow through the introducer needle 25 and into the flashback chamber 38, where it may be visible to a user.

In some embodiments, the plug 26 may plug a proximal opening 40 of the flashback chamber 38 and provide venting of the flashback chamber 38. In some embodiments, the plug 26 may include a distal end 42, a proximal end 44, a lumen 46 extending through the distal end 42 of the plug 26 and the proximal end 44 of the plug 26, and a tubular section 48 disposed between the distal end 42 of the plug 26 and the proximal end 44 of the plug 26. In some embodiments, the distal end 42 of the plug 26 may include a neck portion 50 and/or a skirt 52, which may each extend from the tubular section 48 to define an annular channel 54 between the skirt 52 and the neck portion 50.

In some embodiments, the neck portion 50 may be inserted into the proximal end 30 of the needle hub 24 and may fit securely within the proximal end 30 of the needle hub 24. In some embodiments, an outer surface of the neck portion 50 may include one or more air vent channels 56, which may be configured to provide venting of the flashback chamber 38. In some embodiments, the air vent channels 56 may be configured to pass air but not blood.

In some embodiments, the proximal end 44 of the plug 26 may include a luer adapter 58. In some embodiments, the proximal end 44 of the plug 26 may include a septum 60, which may be disposed within the luer adapter 58. In some embodiments, the air vent channels 56 may facilitate blood flow through the introducer needle and into the flashback chamber and the plug 26. In some embodiments, the plug 26 may facilitate blood collection from the flashback chamber via a blood collection device, which may be connected to the luer adapter 58.

In some embodiments, a method of blood sampling or collecting blood may include inserting the catheter system 10 into vasculature of a patient. In some embodiments, the method may include coupling the blood collection device to the proximal end 44 of the plug 26. In some embodiments, the method may include collecting blood from the vasculature within the blood collection device. In some embodiments, the method may include priming the catheter system 10 prior to insertion of the catheter system 10 into the vasculature.

Figure 1E:
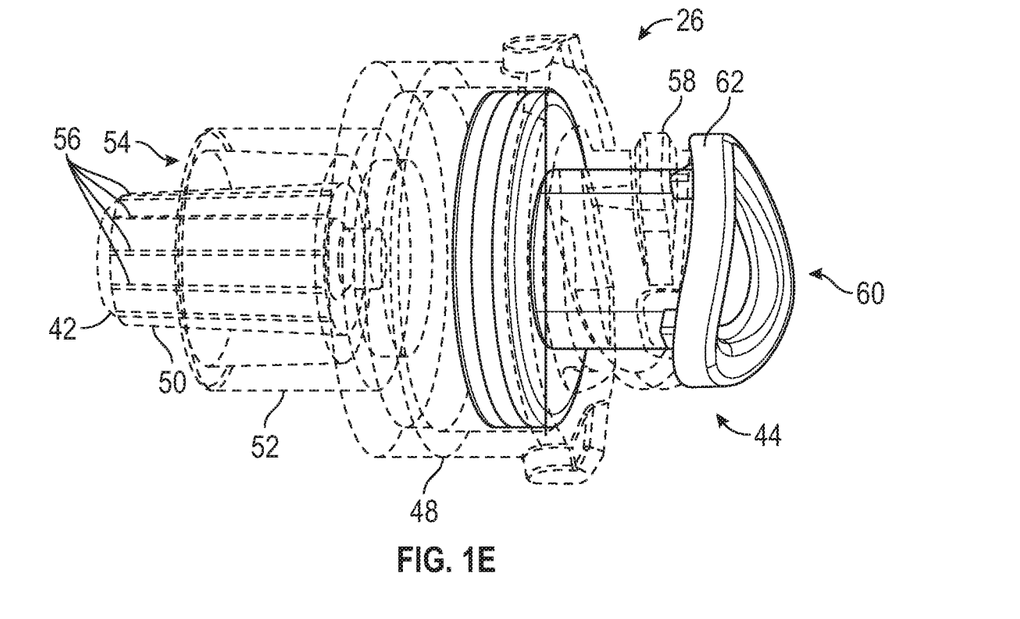
FIG. 1E is an upper perspective view of an example plug, according to some embodiments.
Figure 1F:
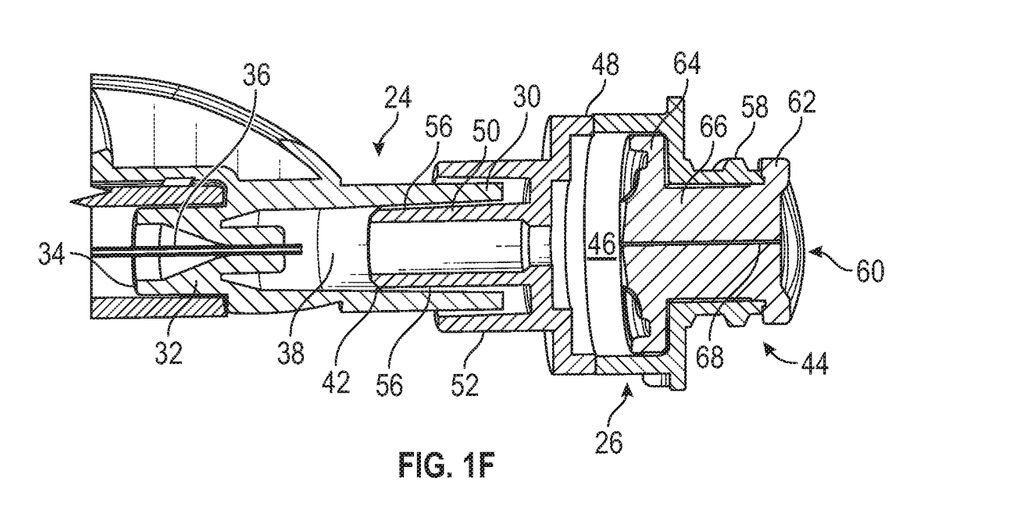
FIG. 1F is a cross-sectional view of the plug of FIG. 1E coupled to the needle hub of FIG. 1B, according to some embodiments.

In some embodiments, the septum 60 may include a proximal portion 62, which may be disposed outside the luer adapter 58. In some embodiments, the septum 60 may include a distal portion 64, which may extend across the tubular section 48. In some embodiments, the septum 60 may include an intermediate portion 66, which may be disposed between the proximal portion 62 and the distal portion 64. In some embodiments, the septum 60 may include a slit 68, which may extend longitudinally through the proximal portion 62, the distal portion 64, and the intermediate portion 66. In some embodiments, a cross-section of the proximal portion 62, the distal portion 64, and the intermediate portion 66 may form a general H-shape. In some embodiments, the distal portion 64 may be pinched within the plug 26 to secure the septum 60 within the plug 26, although it is understood that the septum 60 may be secured within the plug 26 by other means.

Figure 2A:
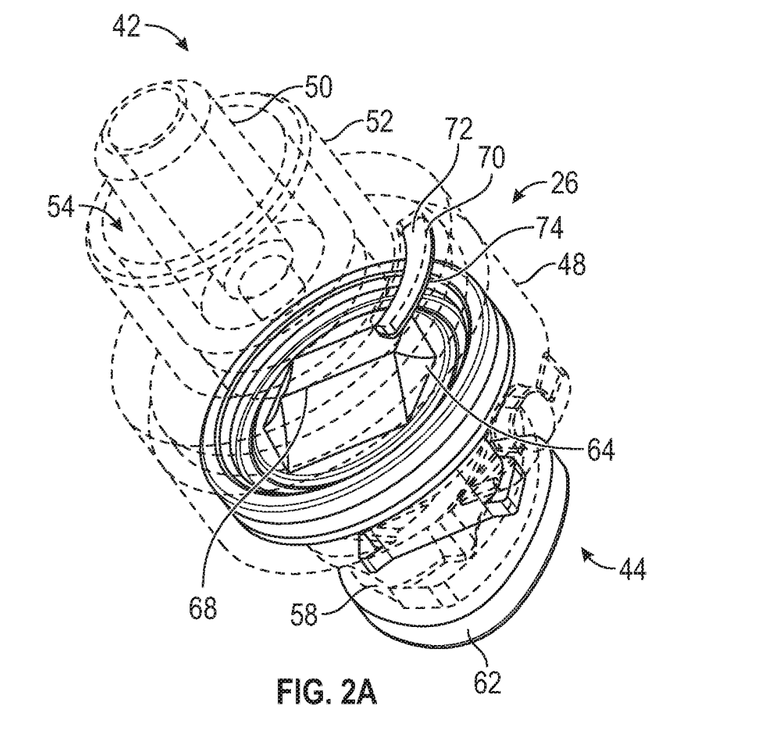
FIG. 2A is a lower perspective view of the plug of FIG. 1E, illustrating an example vent, according to some embodiments.
Figure 2B:
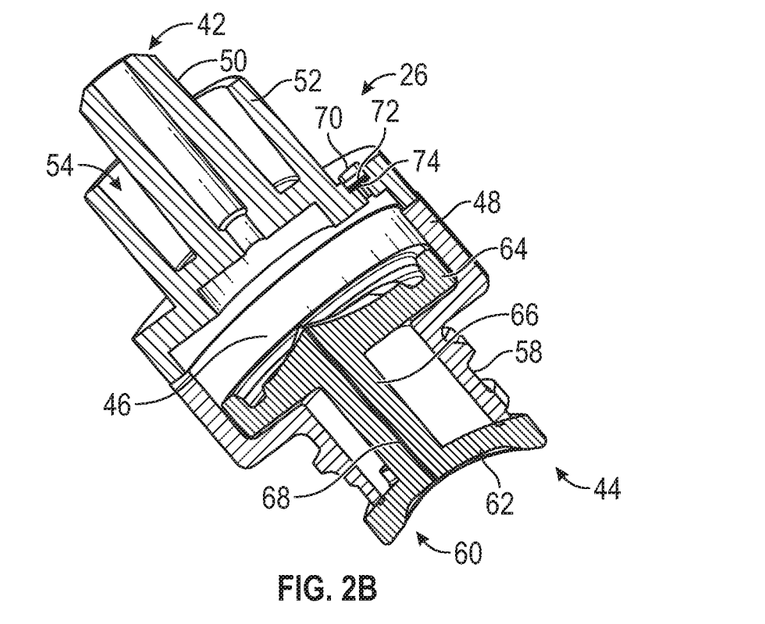
FIG. 2B is a cross-sectional view of the plug of FIG. 2A, according to some embodiments.

Referring now to FIGS. 2A-2B, in some embodiments, a portion of a wall of the tubular section 48 may include a hole 70, which may extend through the wall. In some embodiments, a hydrophobic membrane 72 may be disposed within the hole 70 towards an outside of the plug 26. In some embodiments, a hydrophilic membrane 74 may be disposed within the hole 70 towards an inside of the plug 26 and/or proximate the hydrophobic membrane 72. In some embodiments, the hydrophilic membrane 74 may prevent fluid leakage through the hole 70, and the hydrophobic membrane 72 may provide venting of the flashback chamber. In some embodiments, after the hydrophobic membrane 72 is wetted by blood, it loses its capacity to vent air and becomes a barrier to prevent atmospheric air from entering the plug 26. The blood collection device, such as a tube or syringe, may then be used to collect blood when negative pressure is applied.

In some embodiments, the hole 70 may be distal to the distal portion 64 of the septum 60. In some embodiments, the hole 70 may be elongated and/or arc-shaped along a shape of a flange of the tubular section 48. In some embodiments, the hole 70 may be another suitable shape. In some embodiments, the hydrophobic membrane 72 may facilitate blood flow through the introducer needle and into the flashback chamber and the plug 26.

Figure 3A:
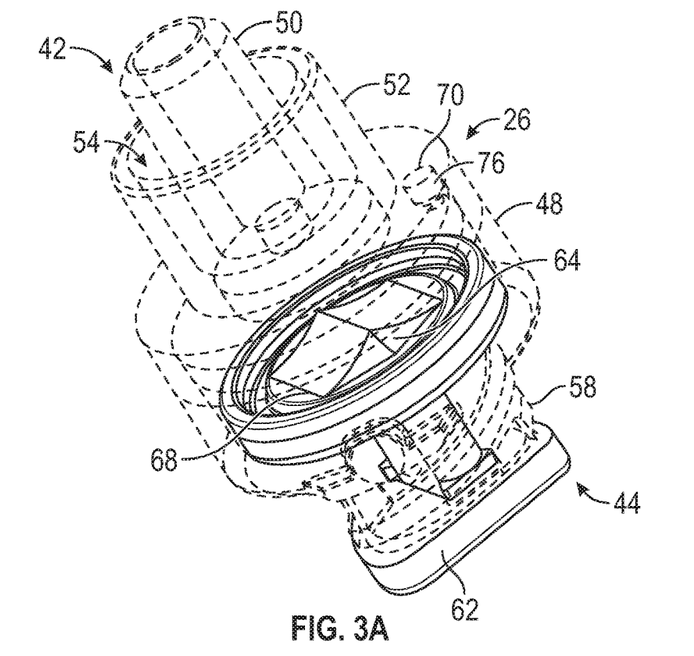
FIG. 3A is a lower perspective view of the plug of FIG. 1E, illustrating another example vent, according to some embodiments.
Figure 3B:
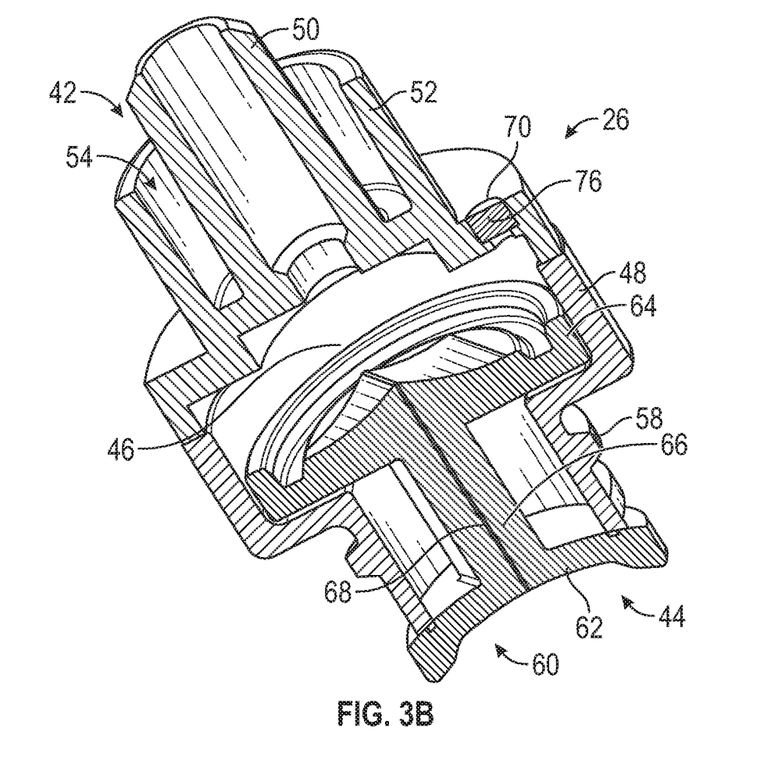
FIG. 3B is a cross-sectional view of the plug of FIG. 3A, according to some embodiments.

Referring now to FIGS. 3A-3B, in some embodiments, as an alternative to the hydrophobic membrane and the hydrophilic membrane described with respect to FIGS. 2A-2B, a porous membrane 76 may be disposed within the hole 70. In some embodiments, the porous membrane 76 may be configured to pass air but not blood. In some embodiments, the porous membrane 76 may facilitate blood flow through the introducer needle 25 and into the flashback chamber and the plug 26.

Referring now to FIGS. 4A-4D, a catheter system 78 may be similar or identical to the catheter system 10 described with respect to FIGS. 1A-3B in terms of one or more included components and/or operation. In some embodiments, the catheter system 78 may include a plug 80. In some embodiments, the plug 80 may be similar or identical to the plug 26 described with respect to FIGS. 1A-3B in terms of one or more included components and/or operation. In some embodiments, the needle hub 24 may be configured to insert into the catheter adapter 14, as illustrated, for example, in FIGS. 1B-1D. In other embodiments, the catheter adapter 14 may be configured to insert into a distal cavity 82 of the needle hub 24, as illustrated, for example, in FIGS. 4B-4D.

Figure 4A:
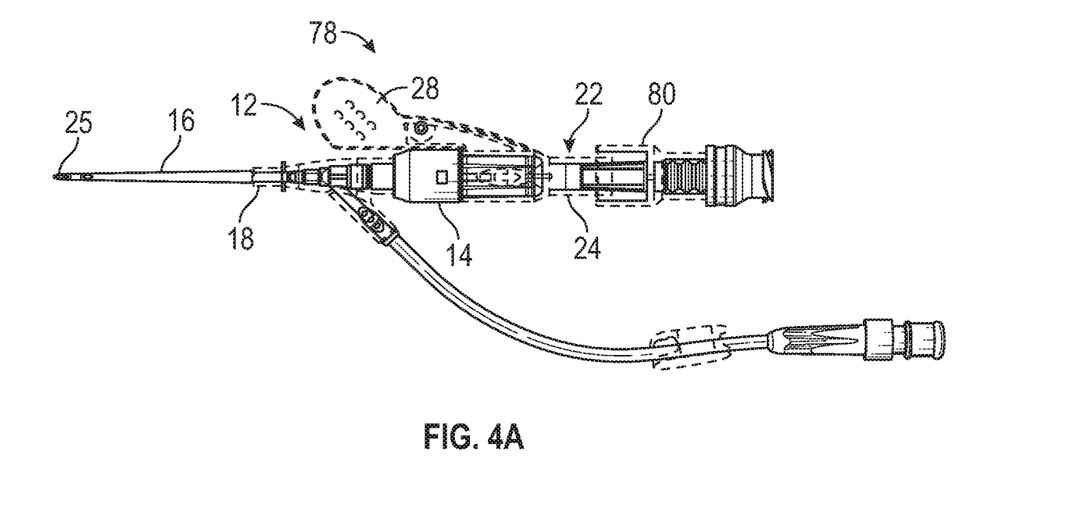
FIG. 4A is an upper perspective view of another example catheter system in the insertion configuration ready for insertion into the patient, according to some embodiments.
Figure 4B:
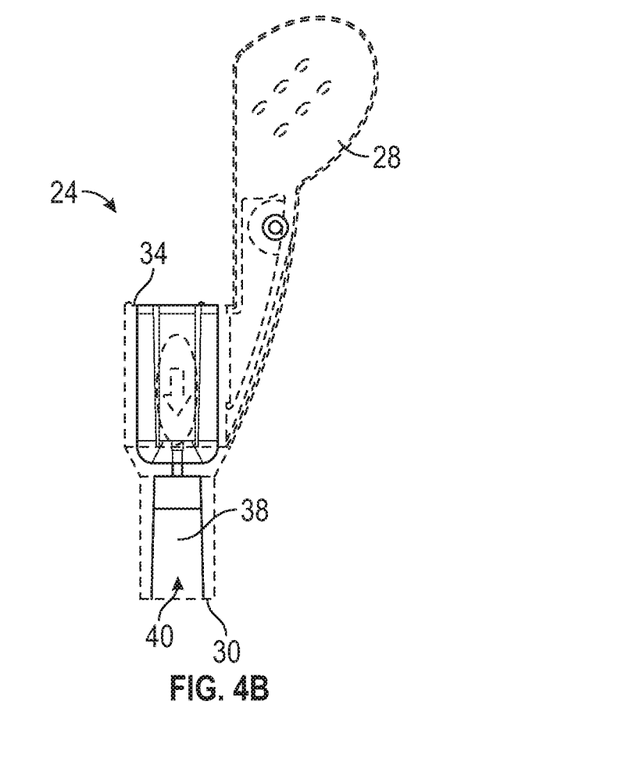
FIG. 4B is an upper perspective view of another example needle hub, with an example introducer needle removed, according to some embodiments.
Figure 4C:
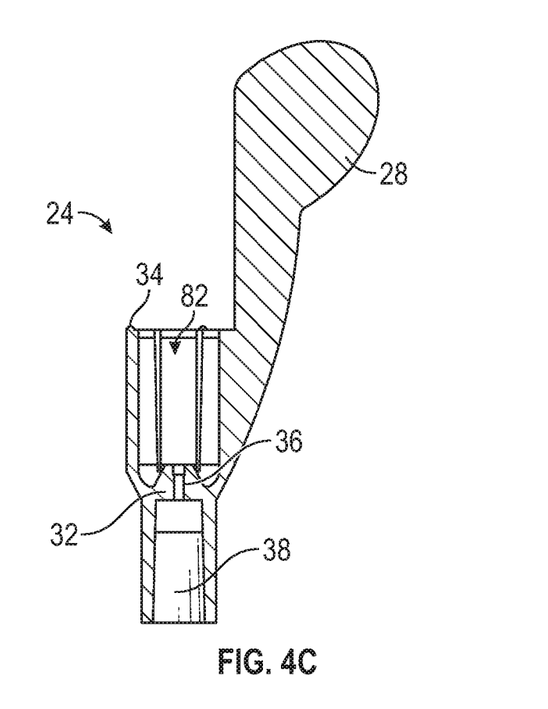
FIG. 4C is a cross-sectional view of the needle hub of FIG. 4B, according to some embodiments.
Figure 4D:
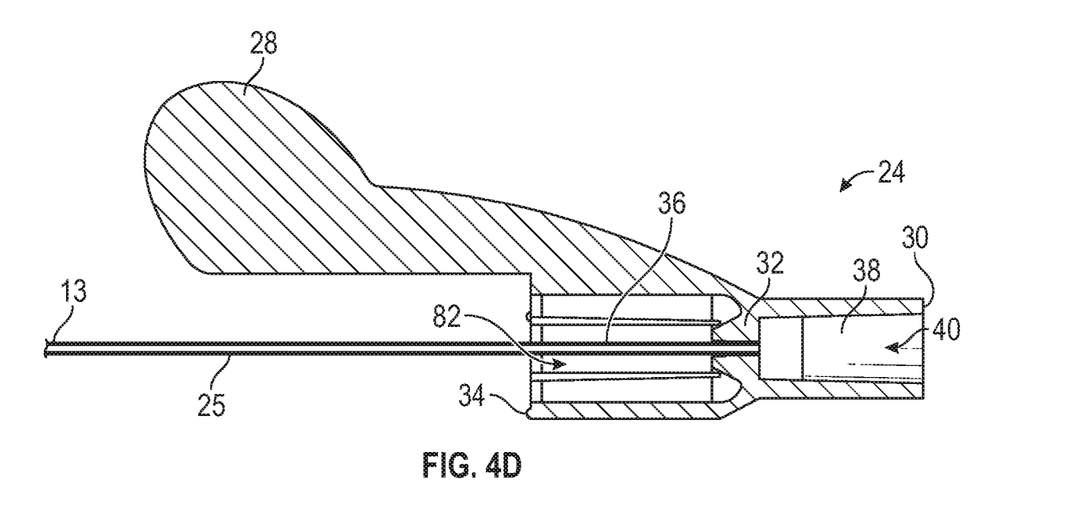
FIG. 4D is a cross-sectional view of the needle hub of FIG. 4B, illustrating the introducer needle press-fit within an example through-hole of the needle hub, according to some embodiments.
Figure 4E:
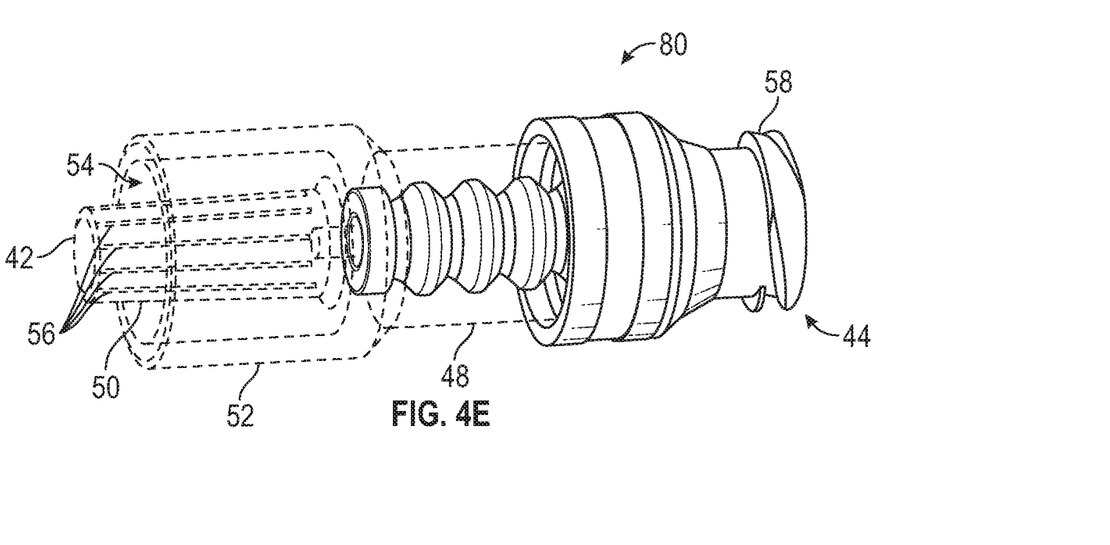
FIG. 4E is an upper perspective view of another example plug, according to some embodiments.
Figure 4F:
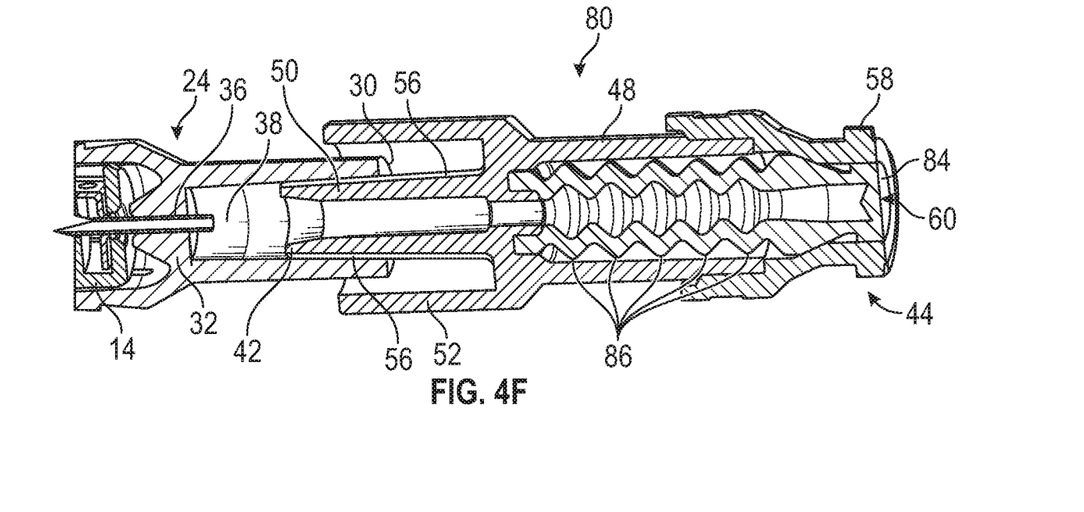
FIG. 4F is a cross-sectional view of the plug of FIG. 4E coupled to the needle hub of FIG. 4B, according to some embodiments.

Referring now to FIGS. 4E-4F, in some embodiments, a septum 60 of the plug 80 may include a resiliently deformable piston element. In some embodiments, the piston element comprises a piston head 84 coupled to one or more bellows 86, which may form an accordion shape. In some embodiments, the piston head 84 may include a slit or bore. In some embodiments, in response to coupling of the blood collection device to the luer adapter 58, the piston head 84 may move distally and the bellows 86 may compress. In some embodiments, in response to compression of the bellows 86, the septum 60 may open to allow blood to flow through the septum 60 and into the blood collection device.

Figure 5A:
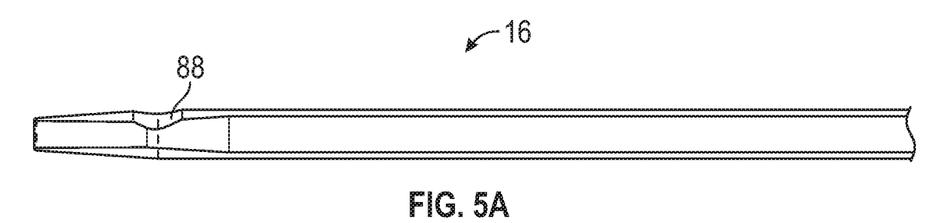
FIG. 5A is a cross-sectional view of an example catheter, according to some embodiments.
Figure 5B:
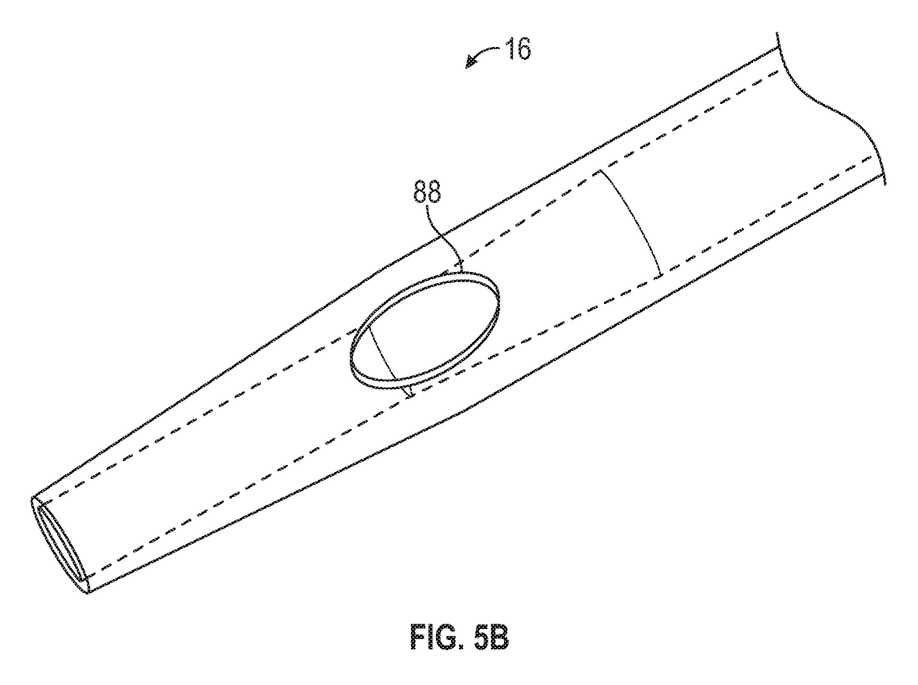
FIG. 5B is a top view of the catheter of FIG. 5B, according to some embodiments.

Referring now to FIGS. 5A-5B, in some embodiments, a distal end of the catheter 16 may include a hole or notch 88 configured to receive blood in response to insertion of the distal end of the catheter 16 into the vasculature of the patient. In some embodiments, the catheter system 10 and/or the catheter system 78 may include the catheter 16 having the notch 88. In some embodiments, the notch 88 may be in fluid communication with the flashback chamber. In further detail, in some embodiments, blood may flow into the notch 88 and between an inner surface of the catheter 16 and the introducer needle in a proximal direction. Blood may exit the proximal end of the introducer needle, flow into the flashback chamber, and then flow into the plug 26 described with respect to FIGS. 1A-3B or the plug 80 described with respect to FIGS. 4A-4F.

In some embodiments, the distal end of the catheter 16 may include the notch 88 in fluid communication with the flashback chamber, and the blood from the vasculature may be collected within the blood collection device without a discard blood sample. In some embodiments, the discard blood sample may not be necessary because priming solution may not enter the introducer needle due to the notch 88 being in the catheter 16 as opposed to the introducer needle.

Figure 6:
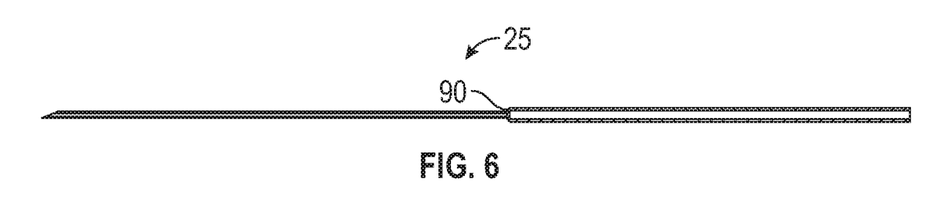
FIG. 6 is a cross-sectional view of an example introducer needle, according to some embodiments.

Referring now to FIG. 6, in some embodiments, the introducer needle 25 may include multiple inner diameters. In some embodiments, an inner surface of the introducer needle 25 may include one or more stepped portions 90 at which an inner diameter of the introducer needle 25 may increase. In some embodiments, the stepped portions 90 may facilitate increased blood flow through the introducer needle 25. In some embodiments, the catheter system 10 and/or the catheter system 78 may include the introducer needle 25 having the stepped portions 90.

The present invention may be embodied in other specific forms without departing from its structures, methods, or other essential characteristics as broadly described herein and claimed hereinafter. The described embodiments are to be considered in all respects only as illustrative, and not restrictive. The scope of the invention is, therefore, indicated by the appended claims, rather than by the foregoing description. All changes that come within the meaning and range of equivalency of the claims are to be embraced within their scope.

We claim:

1. A catheter system, comprising:
   a catheter assembly, comprising:
      a catheter adapter, comprising a distal end, a proximal end, and a lumen extending through the distal end of the catheter adapter and the proximal end of the catheter adapter; and
      a catheter secured within the catheter adapter and extending distally from the distal end of catheter adapter; and
   a needle assembly, comprising:
      a needle hub, comprising:
         a distal end coupled to the proximal end of the catheter adapter;
         a proximal end;
         a wall extending between the distal end of the needle hub and the proximal end of the needle hub;
         a flashback chamber proximate the wall and extending through the proximal end of the needle hub; and
         a through-hole disposed at a distal end of the flashback chamber and within the wall;
      an introducer needle comprising a proximal end having an outer diameter greater than a diameter of the through-hole, wherein the introduce needle is press-fit within the through-hole; and
      a plug coupled to the proximal end of the needle hub, wherein the plug plugs a proximal opening of the flasback chamber and provides venting of the flasback chamber, wherein the plug comprises a distal end, a proximal end, a lumen extending through the distal end of the plug and the proximal end of the plug, wherein the proximal end of the plug comprises a luer adapter and a septum disposed with the luer adapter.

2. The catheter system of claim 1, wherein the plug further comprises a tubular section disposed between the distal end of the plug and the proximal end of the plug, wherein the distal end of the plug comprises a neck portion extending from the tubular section and a skirt extending from the tubular section to define an annular channel between the skirt and the neck portion, wherein the neck portion is inserted into the proximal end of the needle hub, wherein an outer surface of the neck portion comprises a plurality of air vent channels configured to provide venting of the flashback chamber.

3. The catheter system of claim 2, wherein the septum comprises a resiliently deformable piston element, wherein the resiliently deformable piston element comprises a piston head coupled to a plurality of bellows, wherein the piston head comprises a slit or bore.

4. The catheter system of claim 1, wherein the plug further comprises a tubular section disposed between the distal end of the plug and the proximal end of the plug, wherein the distal end of the plug comprises a neck portion extending from the tubular section and a skirt extending from the tubular section to define an annular channel between the skirt and the neck portion, wherein the neck portion is inserted into the proximal end of the needle hub, wherein a portion of a wall of the tubular section comprises a hole, a hydrophobic membrane disposed within the hole towards an outside of the plug, and a hydrophilic membrane within the hole towards an inside of the plug, wherein the hydrophilic membrane prevents fluid leakage through the hole, wherein the hydrophobic membrane provides venting of the flashback chamber.

5. The catheter system of claim 4, wherein the septum comprises a proximal portion disposed outside the luer adapter, a distal portion extending across the tubular section, an intermediate portion between the proximal portion and the distal portion, and a slit extending longitudinally through the proximal portion, the distal portion, and the intermediate portion, wherein a cross-section of the proximal portion, the distal portion, and the intermediate portion forms a general H-shape, wherein the hole is distal to the distal portion of the septum.

6. The catheter system of claim 1, wherein the plug further comprises a tubular section disposed between the distal end of the plug and the proximal end of the plug, wherein the distal end of the plug comprises a neck portion extending from the tubular section and a skirt extending from the tubular section to define an annular channel between the skirt and the neck portion, wherein the neck portion is inserted into the proximal end of the needle hub, wherein a portion of a wall of the tubular section comprises a hole, wherein a porous membrane is disposed within the hole, wherein the porous membrane is configured to pass air but not blood.

7. The catheter system of claim 6, wherein the septum comprises a proximal portion disposed outside the luer adapter, a distal portion extending across the tubular section, an intermediate portion between the proximal portion and the distal portion, and a slit extending longitudinally through the proximal portion, the distal portion, and the intermediate portion, wherein a cross-section of the proximal portion, the distal portion, and the intermediate portion forms a general H-shape, wherein the hole is distal to the distal portion of the septum.

8. The catheter system of claim 1, wherein a distal end of the catheter comprises a notch, wherein the notch is in fluid communication with the flashback chamber.

9. The catheter system of claim 1, wherein the needle assembly further comprises a grip extending outwardly from the needle hub and distal to the distal end of the needle hub.

10. The catheter system of claim 1, wherein the wall is monolithically formed as a single unit.

11. A method of collecting blood, comprising:
inserting a catheter system into vasculature of a patient, wherein the catheter system comprises:
  a catheter assembly, comprising:
    a catheter adapter, comprising a distal end, a proximal end, and a lumen extending through the distal end of the catheter adapter and the proximal end of the catheter adapter; and
    a catheter secured within the catheter adapter and extending distally from the distal end of catheter adapter;
  a needle assembly, comprising:
    a needle hub, comprising:
      a distal end coupled to the proximal end of the catheter adapter;
      a proximal end;
      a flashback chamber extending through the proximal end of the needle hub; and
      a through-hole disposed at a distal end of the flashback chamber; and
    an introducer needle press-fit within the through-hole; and
    a plug coupled to the proximal end of the needle hub, wherein the plug plugs a proximal opening of the flashback chamber and provides venting of the flashback chamber, wherein the plug comprises distal end, a proximal end, a lumen extending through the distal end of the plug and the proximal end of the plug, and a tubular section disposed between the distal end of the plug and the proximal end of the plug, wherein the distal end of the plug comprises a neck portion extending from the tubular section and a skirt extending from the tubular section to define an annular channel between the skirt and the neck portion, wherein the neck portion is inserted into the proximal end of the needle hub, wherein the proximal end of the plug comprises a luer adapter and a septum disposed within the luer adapter;
coupling a blood collection device to the proximal end of the plug; and
collecting blood from the vasculature within the blood collection device.

12. The method of claim 11, further comprising priming the catheter system prior to insertion of the catheter system into the vasculature.

13. The method of claim 12, wherein a distal end of the catheter comprises a notch, wherein the notch is in fluid communication with the flashback chamber, wherein the blood from the vasculature is collected within the blood collection device without a discard blood sample.

14. The method of claim 11, wherein the septum comprises a resiliently deformable piston element, wherein the resiliently deformable piston element comprises a piston head coupled to a plurality of bellows, wherein the piston head comprises a slit or bore.

15. The method of claim 11, wherein the plug comprises a distal end, a proximal end, a lumen extending through the distal end of the plug and the proximal end, and a tubular section disposed between the distal end of the plug and proximal end of the plug, wherein the distal end of the plug comprises a neck portion extending from the tubular section and a skirt extending from the tubular section to define an annular channel between the skirt and the neck portion, wherein the neck portion is inserted into the proximal end of the needle hub, wherein the proximal end comprises a luer adapter and a septum disposed within the luer adapter, wherein a portion of a wall of the tubular section comprises a hole, a hydrophobic membrane disposed within the hole towards an outside of the plug, and a hydrophilic membrane within the hole towards an inside of the plug, wherein the hydrophilic membrane prevents fluid leakage through the hole, wherein the hydrophobic membrane provides venting of the flashback chamber.

16. The method of claim 15, wherein the septum comprises a proximal portion disposed outside the luer adapter, a distal portion extending across the tubular section, an intermediate portion between the proximal portion and the distal portion, and a slit extending longitudinally through the proximal portion, the distal portion, and the intermediate portion, wherein a cross-section of the proximal portion, the distal portion, and the intermediate portion forms a general H-shape, wherein the hole is distal to the distal portion of the septum.

17. The method of claim 11, wherein the plug comprises a distal end, a proximal end, and tubular section disposed between the distal end of the plug and the proximal end of the plug, wherein the distal end of the plug comprises a neck portion extending from the tubular section and a skirt extending from the tubular section to define an annular channel between the skirt and the neck portion, wherein the neck portion is inserted into the proximal end of the needle hub, wherein the proximal end comprises a luer adapter and a septum disposed within the luer adapter, wherein a portion of a wall of the tubular section comprises a hole, wherein a porous membrane is disposed within the hole, wherein the porous membrane is configured to pass air but not blood.

18. The method of claim 17, wherein the septum comprises a proximal portion disposed outside the luer adapter, a distal portion extending across the tubular section, an intermediate portion between the proximal portion and the distal portion, and a slit extending longitudinally through the proximal portion, the distal portion, and the intermediate portion, wherein a cross-section of the proximal portion, the distal portion, and the intermediate portion forms a general H-shape, wherein the hole is distal to the distal portion of the septum.

19. The method of claim 11, wherein the needle assembly further comprises a grip extending outwardly from the needle hub and distal to the distal end of the needle hub.

* * * * *